United States Patent
Rubin et al.

(10) Patent No.: US 12,394,507 B1
(45) Date of Patent: *Aug. 19, 2025

(54) USER INTERFACE FOR PROVIDING DRUG PRICING INFORMATION

(71) Applicant: WALGREEN CO., Deerfield, IL (US)

(72) Inventors: Jason Rubin, Libertyville, IL (US); Ekta Anand, Schaumburg, IL (US)

(73) Assignee: WALGREEN CO., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/397,442

(22) Filed: Dec. 27, 2023

Related U.S. Application Data

(63) Continuation of application No. 18/111,021, filed on Feb. 17, 2023, now Pat. No. 11,901,055, which is a
(Continued)

(51) Int. Cl.
 *G16H 15/00* (2018.01)
 *G06F 3/0482* (2013.01)
 (Continued)

(52) U.S. Cl.
 CPC ........... *G16H 15/00* (2018.01); *G06F 3/0482* (2013.01); *G06F 21/6218* (2013.01);
 (Continued)

(58) Field of Classification Search
 CPC ........ G16H 15/00; G16H 10/60; G16H 20/10; G16H 40/20; G16H 50/70; G16H 70/40;
 (Continued)

(56) References Cited

U.S. PATENT DOCUMENTS

| | | | |
|---|---|---|---|
| 2014/0039911 A1* | 2/2014 | Iyer | G06Q 30/0207 |
| | | | 705/2 |
| 2020/0294640 A1* | 9/2020 | Ginsburg | G16H 40/20 |
| 2021/0074401 A1 | 3/2021 | Bezdek et al. | |

OTHER PUBLICATIONS

Blue Cross NC, Copayment Tier Definitions, Jan. 16, 2018, https://www.bluecrossnc.com/understanding-health-insurance/how-drug-benefits-work/copayment-tier-definitions (Year: 2018).*

(Continued)

*Primary Examiner* — Joy Chng
(74) *Attorney, Agent, or Firm* — MARSHALL, GERSTEIN & BORUN LLP; Randall G. Rueth

(57) ABSTRACT

Methods and systems are disclosed providing drug pricing information for display on a graphical user interface (GUI). The methods and systems may receive an electronic request from an electronic device that includes information that identifies the user and a prescription drug. The systems and methods transmit the information and an overriding indicator to a database management module configured to access information for the prescription drug, and prevent access to the drug pricing information without additional information unless the overriding indicator is received. Based upon the information and the overriding indicator, the systems and methods determine drug pricing information for the prescription drug, which includes a cash price for the prescription drug. The systems and methods generate a notification that includes the drug pricing information, and transmit the notification to the electronic device for display via the GUI.

20 Claims, 5 Drawing Sheets

Related U.S. Application Data continuation of application No. 17/088,792, filed on Nov. 4, 2020, now Pat. No. 11,610,655.

(51) Int. Cl.
| | | |
|---|---|---|
| *G06F 21/62* | (2013.01) | |
| *G06Q 10/10* | (2023.01) | |
| *G06Q 30/0201* | (2023.01) | |
| *G06Q 40/08* | (2012.01) | |
| *G16H 10/60* | (2018.01) | |
| *G16H 20/10* | (2018.01) | |
| *G16H 40/20* | (2018.01) | |
| *G16H 50/70* | (2018.01) | |
| *G16H 70/40* | (2018.01) | |

(52) U.S. Cl.
CPC ......... *G06Q 10/10* (2013.01); *G06Q 30/0206* (2013.01); *G06Q 40/08* (2013.01); *G16H 10/60* (2018.01); *G16H 20/10* (2018.01); *G16H 40/20* (2018.01); *G16H 50/70* (2018.01); *G16H 70/40* (2018.01)

(58) Field of Classification Search
CPC ... G06F 3/0482; G06F 21/6218; G06Q 10/10; G06Q 30/0206; G06Q 40/08
USPC .......................................................... 705/2–3
See application file for complete search history.

(56) References Cited

OTHER PUBLICATIONS

Blue Cross NC, Copayment Tier Definitions, Jan. 16, 2018, https://www.bluecrossnc.com/understanding-health-insurance/how-drug-benefits-work/cogayment-tier-definitions (Year: 2018).

\* cited by examiner

USER INTERFACE FOR PROVIDING DRUG PRICING INFORMATION

CROSS-REFERENCE TO RELATED APPLICATION

This application is a continuation of U.S. patent application Ser. No. 18/111,021, entitled User Interface for Providing Drug Pricing Information, filed Feb. 17, 2023, which is a continuation of U.S. patent application Ser. No. 17/088,792, entitled User Interface for Providing Drug Pricing Information, filed Nov. 4, 2020, the disclosures of which are incorporated herein in their entireties by reference.

TECHNICAL FIELD

This disclosure generally relates to a system and methods for displaying prescription drug pricing information on a graphical user interface (GUI).

BACKGROUND

When a patient receives a prescription from a prescriber (e.g., the patient's doctor), the patient takes the prescription to the pharmacy to be filled. Once the pharmacy receives the prescription, and prior to it being filled, the pharmacy typically submits the prescription for approval by the payer or pharmacy benefit manager (PBM), such as the customer's (i.e., the patient's) insurance company. In this manner, assuming that the payer approves the prescription, the pharmacist only charges the customer the amount of his or her co-pay, or the remaining amount after the payer pays its portion.

In some scenarios, the patient may desire to know the price of a prescription drug before efforts are made to acquire a prescription from the patient's doctor for the prescription drug. For example, if the patient is aware of the price of prescription drug X and prescription drug Y ahead of the doctor's visit, the patient may be able to ask the doctor to prescribe the cheaper prescription drug X if both are suitable prescription drugs for the patient. In some other scenarios, the patient may desire to know the price of a prescription drug after leaving the doctor's office with a prescription in hand. For example, if the patient takes the prescription for prescription drug Y to the pharmacy and finds out that the price exceeds the patient's budget, the patient may desire to know the price of prescription drug X, which was also discussed at the doctor's office as an alternative prescription drug but not prescribed to the patient.

However, conventional price look-up solutions are typically tailored to inform patients of the cash price for over-the-counter drugs (i.e., drugs that do not require a prescription). Further, pharmacies typically require a prescription for a prescription drug from the patient in order to share the price information for that prescription drug to the patient. As such, conventional price look-up solutions that are designed to provide pricing information to a patient do not have a mechanism for retrieving certain prices, such as co-pay prices, for prescription drugs without receiving corresponding prescriptions for those prescription drugs from the patient, and for displaying such prices to the patient via a user interface.

SUMMARY

In one embodiment, a server for providing drug pricing information for display on a graphical user interface (GUI) executing on an electronic device for a user is provided. The server includes one or more processors configured to: (1) receive an electronic request from an electronic device associated with the user, wherein the electronic request includes information that identifies the user, and a prescription drug; (2) transmit the information and an overriding indicator to a database management module that is configured to interact with a database to access information for the prescription drug stored in the database, the database management module further configured to prevent access to the drug pricing information without additional information unless the overriding indicator is received; (3) determine, based upon the information and the overriding indicator, the drug pricing information for the prescription drug, wherein the drug pricing information includes at least a cash price for the prescription drug identified in the information; (4) generate, in response to the electronic request, a notification that includes the drug pricing information for display via the GUI executing on the electronic device; and (5) transmit the notification to the electronic device via a communication network.

In another embodiment, a computer-implemented method of providing drug pricing information for display on a GUI for a user is provided. The computer-implemented method includes: (1) receiving, by one or more processors, an electronic request from an electronic device associated with the user, wherein the electronic request includes information that identifies the user, and a prescription drug; (2) transmitting, by the one or more processors, the information and an overriding indicator to a database management module that is configured to interact with a database to access information for the prescription drug stored in the database, the database management module further configured to prevent access to the drug pricing information without additional information unless the overriding indicator is received; (3) determining, by the one or more processors based upon the information and the overriding indicator, the drug pricing information for the prescription drug, wherein the drug pricing information includes at least a cash price for the prescription drug identified in the information; (4) generating, by the one or more processors based upon the electronic request, a notification that includes the drug pricing information for display via the GUI executing on the electronic device; and (5) transmitting, by the one or more processors, the notification to the electronic device via a communication network.

In yet another embodiment, a non-transitory, tangible computer-readable medium storing machine readable instructions to provide drug pricing information for display on a GUI for a user is provided. The machine readable instructions, when executed by a processor, cause the processor to: (1) receive an electronic request from an electronic device associated with the user, wherein the electronic request includes information that identifies the user, and a prescription drug; (2) transmit the information and an overriding indicator to a database management module that is configured to interact with a database to access information for the prescription drug stored in the database, the database management module further configured to prevent access to the drug pricing information without additional information unless the overriding indicator is received; (3) determine, based upon the information and the overriding indicator, the drug pricing information for the prescription drug, wherein the drug pricing information includes at least a cash price for the prescription drug identified in the information; (4) generate, in response to the electronic request, a notification that includes the drug pricing information for display via the GUI executing on the electronic device; and (5) transmit the notification to the electronic device via a communication network.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed embodiments and explain various principles and advantages of those embodiments.

Figure 1:
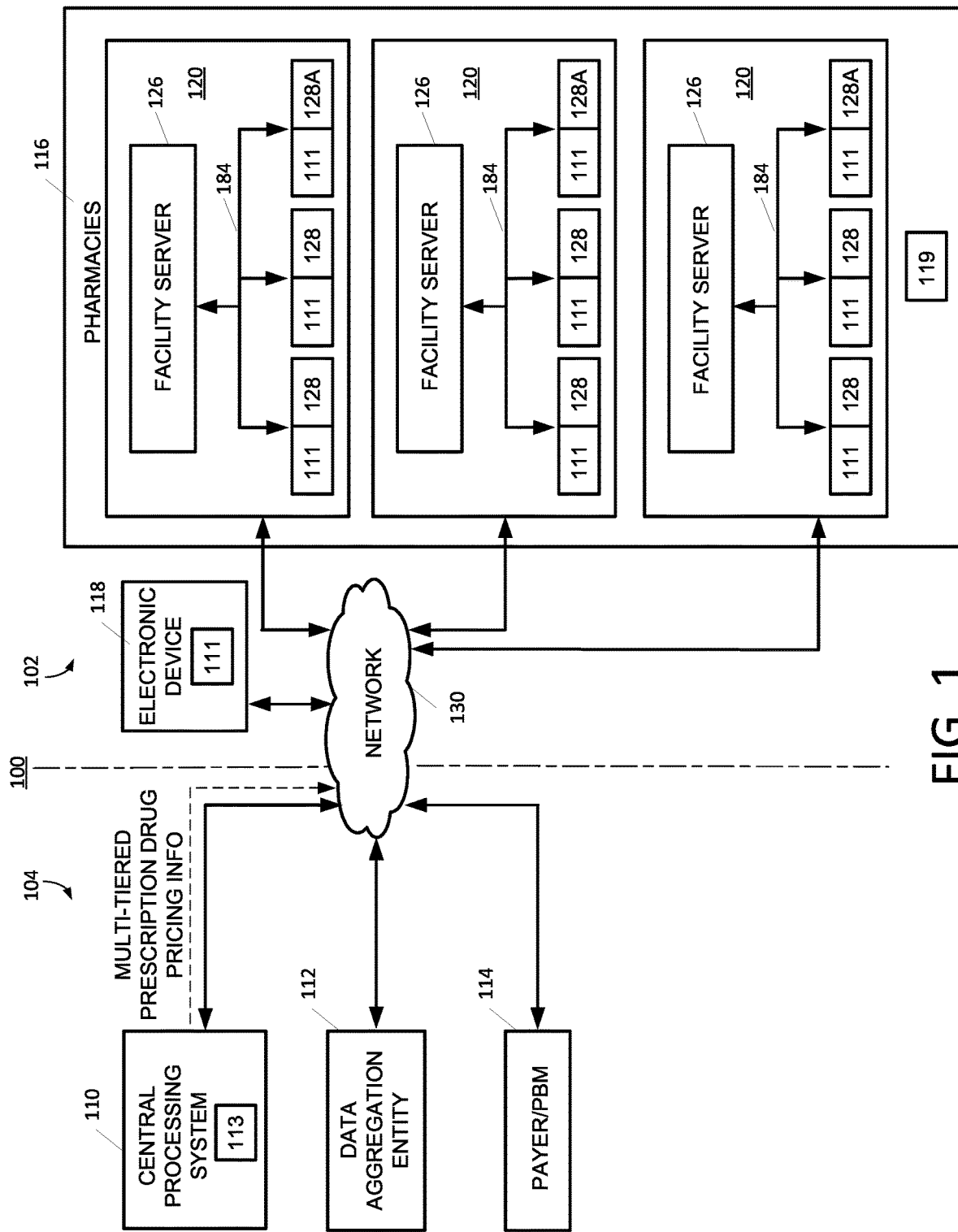
FIG. 1 illustrates a block diagram of a computer network and system on which an exemplary automated prescription drug multi-tiered pricing system and methods thereof may operate in accordance with the described embodiments.

While the systems and methods disclosed herein is susceptible of being embodied in many different forms, it is shown in the drawings and will be described herein in detail specific exemplary embodiments thereof, with the understanding that the present disclosure is to be considered as an exemplification of the principles of the systems and methods disclosed herein and is not intended to limit the systems and methods disclosed herein to the specific embodiments illustrated. In this respect, before explaining at least one embodiment consistent with the present systems and methods disclosed herein in detail, it is to be understood that the systems and methods disclosed herein is not limited in its application to the details of construction and to the arrangements of components set forth above and below, illustrated in the drawings, or as described in the examples.

Methods and apparatuses consistent with the systems and methods disclosed herein are capable of other embodiments and of being practiced and carried out in various ways. Also, it is to be understood that the phraseology and terminology employed herein, as well as the abstract included below, are for the purposes of description and should not be regarded as limiting.

DETAILED DESCRIPTION

A system and methods for displaying prescription drug pricing information on an improved graphical user interface (GUI) are disclosed herein. The improved GUI disclosed herein improves upon conventional GUIs, which do not have technical back-end support for presenting multi-tiered prescription drug pricing (e.g., a cash price and a secondary price, such as a co-pay price or membership price) for a prescription drug without a valid prescription from a prescriber (e.g., physician) for the prescription drug. The improved GUI is supported, for example, by a database schema that enables access to multi-tiered prescription drug pricing information, without requiring a prescription for the prescription drug. In turn, with the multi-tiered prescription drug pricing information available for access, one or more processors can generate a notification that includes the multi-tiered prescription drug pricing information, which can be rendered on the improved GUI. Advantageously, the GUI described herein is not limited to displaying a limited set of information (e.g., single-tiered drug pricing for an over-the-counter drug) to the user, resulting in an improved user interface for electronic devices. Accordingly, the improved GUI can display an expanded set of drug pricing information to the user, thereby equipping the user with additional information for making more-informed health decisions.

As used herein, the term "customer" or "user" indicates a patient (i.e., the person for whom a prescription drug is for), a guardian (e.g., the parent of a child for whom a prescription drug is for), a care-giver (i.e., anyone who takes care of a patient or picks up a drug or medication on the patient's behalf), etc. The "customer" can also be someone purchasing a retail product. Moreover, the term "customer" is not limited to a single person, but may instead be any person or persons having a reason or desire to purchase one or more retail products or prescription drugs, whether the prescription drugs are related to a single patient or multiple patients. For example, a customer could be a caregiver responsible for patients with a specific disease that progresses in a known manner. The caregiver customer might greatly benefit from gaining information related to various prescription drugs and/or health products to assist in his or her caregiver responsibilities. In any event, the term "customer" may be used interchangeably with the term "patient" or "user."

As used herein, the term "pharmacy" indicates an individual pharmacy location or venue within the system, and particularly, the location where the prescription in question has been sent to be filled.

As used herein, the term "prescriber" indicates the physician, nurse practitioner, or other properly licensed healthcare provider that can issue a prescription. Generally, the term prescriber refers to an individual person that authorized the prescription, but it may refer to the related healthcare organization or entity for whom that individual person was performing services in certain instances.

The term "third-party payer" or simply "payer" traditionally indicates an entity to which a prescription is submitted for payment authorization. Typically, the payer is the primary healthcare insurance provider of the customer, but it may alternatively be an agency such as Medicare or some other government organization, a pharmacy benefit manager (PBM), a prescription savings club, a corporation, a pre-paid card or discount card management agency, or an intermediary benefits management agency that administers healthcare-based aspects of a cafeteria plan. As used herein, the payer can receive a request for prescription drug pricing information for a particular prescription drug from the pharmacy or customer, and consequently provide the prescription drug pricing information to the pharmacy or customer without requiring a prescription for that particular prescription drug from the pharmacy or customer.

Generally, the automated prescription drug multi-tiered pricing system as described herein can coordinate data communication with various entities to provide prescription drug pricing information of prescription drug(s) for display on a graphical user interface (GUI), without requiring a prescription(s) for those prescription drug(s) from the customer. The GUI can present the prescription drug pricing information in an easily digestible manner, so that the customer can easily view and understand multiple prices applicable to a desired prescription drug. For example, each price may be labeled to designate what the price represents, and why the prices are different. The prescription drug pricing information can include a "cash price" for the prescription drug(s), a "co-pay price" for the prescription drug(s), a "membership price" for the prescription drug(s), and/or any other suitable price to be paid by the customer for the prescription drug(s). The cash price is the full retail price for a prescription drug that is not covered by the customer's health insurance plan, or if the customer does not have a health insurance plan. The co-pay price is the fixed out-of-pocket amount for the prescription drug that is covered by the customer's health insurance plan. The membership price is the discounted price for the prescription drug in view of a membership plan, coupon, and/or rewards affiliated with the pharmacy. In some instances, membership price can be the price negotiated with a manufacturer of the prescription drug. In other instances, the membership price can be the cash price or co-pay price for the prescription drug(s) less any discounts. Because the prescription drug pricing information can include multiple prices for the same prescription drug, the prescription drug pricing information is also referred to (and interchangeably used with) "multi-tiered prescription drug pricing information" throughout this disclosure. The prescription drug pricing information can also include the dosage of the prescription drug(s) corresponding to any of the prices discussed above.

FIG. 1 illustrates various aspects of an exemplary architecture implementing the automated prescription drug multi-tiered pricing system 100. The architecture includes both hardware and software applications, as well as various data communications channels for communicating data between the various hardware and software components. The automated prescription drug multi-tiered pricing system 100 may be roughly divided into front-end components 102 and back-end components 104. The front-end components 102 can be disposed within a retail network 116 including one or more pharmacies 120. The pharmacies 120 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 120 throughout the retail network 116 and executing various pharmacy management-related applications. Pharmacists, technicians, and other pharmacy personnel, referred to collectively herein simply as "pharmacists" (not shown), use the pharmacy workstations 128 to access customer information, enter new prescriptions, access insurance and payment information, and access prescription drug pricing information generated by the back-end components 104. Each of the pharmacies 120 may be, for example, an in-store retail pharmacy, an on-line pharmacy, a mail-order pharmacy, a long-term care pharmacy, a workplace/on-site pharmacy, or a specialty pharmacy. The retail network 116 may also include one or more warehouses or central-filling facilities 119. The warehouses or central-filling facilities 119 may distribute medications (i.e., drugs) or retail products to the various retail pharmacies 120 in the retail network 116, or may distribute medications or retail products directly to customers.

Those of ordinary skill in the art will recognize that the front-end components 102 could also comprise a plurality of facility servers 126 and client device terminals 128A disposed at the plurality of pharmacies 120 instead of, or in addition to, a plurality of pharmacy workstations 128. Each of the pharmacies 120 may include one or more facility servers 126 that may facilitate communications between the client device terminals 128A and the back-end components 104 via a digital network 130, and may store information for a plurality of customers, employees, accounts, etc. Of course, a local digital network 184 may also operatively connect each of the workstations 128 to the facility server 126. Unless otherwise indicated, any discussion of the workstations 128 also refers to the facility servers 126 and/or the client device terminals 128A, and vice versa. Moreover, environments other than the pharmacies 120 may employ the workstations 128, the client device terminals 128A, and/or the servers 126. As used herein, the term "pharmacy" refers to any of these environments (e.g., call centers, kiosks, Internet interface terminals, etc.) in addition to the retail pharmacies 120, described above.

An electronic device 118 (e.g., personal computers, cellular phones, smart phones, internet-enabled televisions, etc.) may be communicatively connected to the back end components 104, through the digital network 130. A customer uses the electronic devices 118 to access prescription drug pricing information generated by the back-end components 104, as well as other information, such as of retail products offered at a retailer associated with the pharmacy 120. The electronic device 118 may, but need not be, disposed within the retail network 116. As will be described herein, each of the workstations 128, client device terminals 128A, and/or the electronic devices 118 may execute or run a user interface application 111, through which a pharmacist or customer may initiate and interact with the automated prescription drug multi-tiered pricing system 100. The digital network 130 may support communicative connections between applications 111 executing on the workstations 128, client device terminals 128, and/or the electronic devices 118 and the back-end components 104. For example, the applications 111 may include a web-browser and/or a downloaded retailer client application that communicate with one or more back-end components 104 via the network 130, e.g., to access prescription drug pricing information for display via graphical user interfaces (GUIs).

The front-end components 102 communicate with the back-end components 104 via the digital network 130. One or more of the front-end components 102 may be excluded from communication with the back-end components 104 by configuration or by limiting access due to security concerns. For example, the electronic device 118 may be excluded from direct access or only provided with limited access to the back-end components 104. In some embodiments, the pharmacies 120 may communicate with the back-end components 104 via the same digital network 130. In other embodiments, the pharmacies 120 may communicate with the back-end components 104 via different digital networks 130 communicatively coupled to each other. The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol.

The back-end components 104 include a central processing system 110, a payer or PBM 114, and optionally, a data aggregation entity 112 that facilitates data communication between the central processing system 110 and the payer or PBM 114. In some embodiments, the data aggregation entity 112 can compile, e.g., upon execution of a data aggregation module, prescription drug pricing information from a database at the payer or PBM 114 to prepare datasets in a suitable format for data transmission to the central processing system 110. The central processing system 110 may be a server within a central processing facility (e.g., central-filling facilities 119), or a separate entity, as illustrated. Further, the central processing system 110 may implement a server application 113 for providing multi-tiered prescription drug pricing information data to user interface applications 111 operating on the plurality of pharmacy workstations 128 and/or electronic device 118. Of course, the pharmacies 120 and/or electronic device 118 may be communicatively connected to different back-end components 104 having one or more functions or capabilities that are similar to the central processing system 110. As will be described in FIG. 2, the central processing system 110 may include one or more computer processors 210 adapted and configured to execute various software applications and components of the automated prescription drug multi-tiered pricing system 100, in addition to other software applications.

The customer, or pharmacist on behalf of the customer, via the user interface application 111 executing on the electronic device 118 or pharmacy workstation 128, respectively, can send an electronic request to the central processing system 110 over the digital network 130 to access prescription drug pricing information from the central processing system 110. Information or data stored in the electronic request may include, for example, the customer name, the customer address, the customer birth date, the name of the prescription drug, the quantity of the prescription drug, the days' supply of the prescription drug, insurance or health care plan information of the customer, or other suitable elements. Notably, the information or data stored in the electronic request need not include prescription information or prescriber information. The customer or pharmacist, via the user interface application 111 executing on the electronic device 118 or pharmacy workstation 128, may manually enter any of the elements of the electronic request described above, using an input mechanism (e.g., keyboard) associated with the electronic device 118 or pharmacy workstation 128. In some cases, the user interface application 111 may include optical character recognition (OCR) software capabilities, that would allow the customer or pharmacist to use a character capturing device (e.g., camera, scanner) associated with the electronic device 118 or pharmacy workstation 128 to capture an identification card (e.g., driver's license, insurance card, membership card, etc.), so that the user interface application 111 can automatically detect any of the elements of the electronic request described above without requiring manual entry from the customer or pharmacist.

In some embodiments, in response to receiving the electronic request from the electronic device 118 or pharmacy workstation 128, the central processing system 110 forwards the electronic request (i.e., without additional data processing on the electronic request) directly to the payer (e.g., health insurance provider) or PBM 114 over the digital network 130. In other embodiments, the central processing system 110 can convert the electronic request into a suitable format readable by the payer or PBM 114, if necessary, and subsequently send the converted electronic request directly to the payer or PBM 114. In yet other embodiments, the central processing system 110 can forward the electronic request to an intermediate entity, such as the data aggregation entity 112, which converts the electronic request into a suitable format readable by the payer or PBM 114.

In some embodiments, the electronic device 118, pharmacy workstation 128, central processing system 110, or data aggregation entity 112 may include an price inquiry indicator (e.g., a flag, certain bit(s) set to a certain value, etc.) in the electronic request to designate that the electronic request does not include a prescription corresponding to the prescription drug from a provider. In this way, when the payer or PBM 114 receives the electronic request, the payer or PBM 114 recognizes the price inquiry indicator in the electronic request, and based on the price inquiry indicator, understands that the electronic request is effectively a pricing inquiry (i.e., and not a billing claim for filling a prescription) and thus not missing prescription information. Otherwise, the payer or PBM 114 may reject the electronic request. In other embodiments, the electronic request does not include the price inquiry indicator described above. In these cases, the payer or PBM 114 understands that if the prescription or prescriber information is missing in the electronic request, the electronic request is a pricing inquiry and not a billing claim.

In response to processing (e.g., parsing) the electronic request, the payer or PBM 114 identifies the price(s) for the prescription drug included in the electronic request. In some embodiments, the payer or PBM 114 has access to a database containing information for prices of numerous prescription drugs, and what those prices are under numerous health care plans. Depending on other elements included in the electronic request, such as the quantity of the prescription drug, the days' supply of the prescription drug, insurance or health care plan information of the customer, the prices can differ.

For example, if the electronic request includes the name of the customer and the customer's insurance or health care plan information, the payer or PBM 114 can identify a co-pay price for the prescription drug. The co-pay price may depend on whether the prescription drug is on a formulary list associated with the customer's insurance or health care plan, and the quantity of the prescription drug. Accordingly, the payer or PBM 114 can compare the name of the prescription drug included in the received electronic request with the customer-specific health plan coverage information to determine whether the prescription drug included in the electronic prescription is non-formulary or formulary. The prescription drug included in the electronic prescription may be non-formulary if the prescription drug is not normally covered by an insurance, is a particularly high dose, has significant risk potential, is being used to treat or ameliorate off-label disease(s)/condition(s), or is not usually recommended for a particular age or gender. As another example, if the electronic request only includes the name of the prescription drug without any additional information to determine whether a co-pay price may be applicable for the prescription drug, the payer or PBM 114 can identify a cash price for the prescription drug. Upon determining all of the applicable prices, the payer or PBM 114 may send a notification including the price(s) back to the transmitter of the electronic request (e.g., electronic device 118, pharmacy workstation 128, central processing system 110, or data aggregation entity 112), so that ultimately, the electronic device 118 or pharmacy workstation 128 can proceed with displaying the price(s) for the prescription drug to the customer.

In some embodiments, in response to receiving the electronic request from the electronic device 118 or pharmacy workstation 128, the central processing system 110 need not forward the electronic request to the payer or PBM 114 over the digital network 130. Instead, the central processing system 110 may have direct access to a database containing information for prices of numerous prescription drugs, and what those prices are under numerous health care plans. As such, the central processing system 110 can be capable of processing the electronic request to identify the price(s) for the prescription drug included in the electronic request, similar to the manner in which the payer or PBM 114 identifies the price(s), as discussed above.

Although FIG. 1 depicts the automated prescription drug multi-tiered pricing system 100 as including the central processing system 110 in communication with three pharmacies 120, it should be understood that different numbers of processing systems and pharmacies may be utilized. For example, the digital network 130 (or other digital networks, not shown) may interconnect the central processing system 110 to a plurality of central processing systems 110 and hundreds of pharmacies 120. According to the disclosed example, this configuration may provide several advantages, such as, for example, enabling near real-time uploads and downloads of information as well as periodic uploads and downloads of information. This provides for a primary backup of all the information generated in the automated pharmacy process. Alternatively, some of the pharmacies 120 may store data locally on the facility server 126 and/or the workstations 128.

Figure 2:
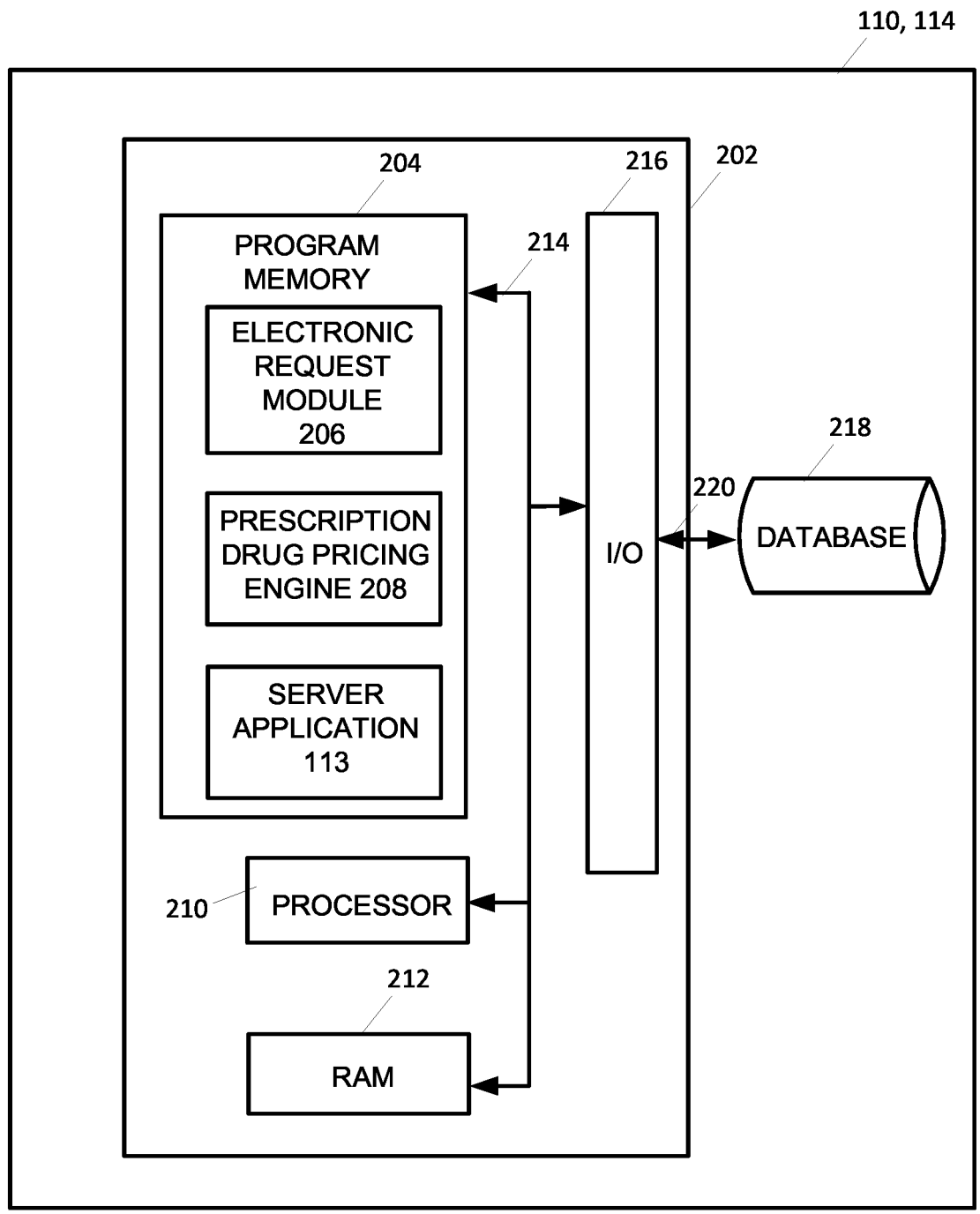
FIG. 2 illustrates a block diagram of a back-end component of the automated prescription drug multi-tiered pricing system in accordance with the described embodiments.

FIG. 2 illustrates various aspects of an exemplary architecture of back-end component 200, which can represent either the central processing system 110 or the payer or PBM 114 depending on the embodiment. For instance, if the central processing system 110 transmits prescription drug information included in the electronic request to the payer or PBM 114 for processing, back-end component 200 represents the payer or PBM 114. If the central processing system 110 processes the electronic request itself without the need to interface with the payer or PBM 114, back-end component 200 represents the central processing system 110. Certain factors may drive one implementation over another. For example, to comply with state, local, federal privacy regulations, and/or contractual agreements or other suitable reasons, the central processing system 110 may not store payer/PBM data, and thus may interface with the payer or PBM 114 to transmit prescription drug information included in the electronic request to the payer or PBM 114.

As shown in FIG. 2, one possible embodiment of the back-end component 200 may include a controller 202 operatively connected to the database 218 via a link 220 connected to an input/output (I/O) circuit 216. It should be noted that, while not shown, additional databases may be linked to the controller 202 in a known manner. The database 218 is adapted to store data related to the customer (e.g., patient profile data, prescriber profile data, customer-specific health plan coverage information data), and/or payer/PBM profile data (e.g., customer-specific health plan coverage information data, various prices for various prescription drugs). The back-end component 200 may access data stored in the database 218 when executing various functions and tasks associated with the operation of the automated prescription drug multi-tiered pricing system 100. For simplicity, FIG. 2 illustrates the database 218 as only one instance of a database. However, the database 218 according to some implementations includes a group of one or more databases, each storing different information. For example, one database may store patient profile data while another may store payer/PBM profile data. For the purposes of this discussion, the term "database" 218 may refer to an individual database or to a group of two or more databases, and/or for a database management module that interacts with entities, applications, and the database itself to capture and access or analyze the data.

The database 218 may include various information about the pharmacy's customers. Customer records are among the exemplary data that the automated prescription drug multi-tiered pricing system 100 may store in the database 218. A customer record contains important information about the customer and the various pharmacy services that have been invoked by, or on behalf of, the customer in a customer profile. The customer profile includes basic biographical information about the customer, such as a customer name, a customer social security number, a customer address, a customer rewards or membership number, a customer phone number, a customer birth date, customer prescription history, customer allergies, customer health plan coverage information, etc. Moreover, customer-specific health plan coverage information records may include a prescription drug name, a size of the prescription drug, a generic equivalent, whether the prescription drug is a controlled substance, a Dispense as Written (DAW) code, a National Drug Code (NDC), patient identification information (benefits information (e.g., covered formulary medication), prior authorization designation information (e.g., whether a certain medication requires prior authorization), adjudicated price information (i.e., the co-pay price to be paid after the payer or PBM has paid according to benefit or coverage requirements), non-adjudicated price information (i.e., cash price of the prescription drug), alternative medication information (e.g., formulary medication that may be substituted for non-formulary medication), or alternative medication prices information (e.g., the price of formulary medication that may be substituted for non-formulary medication). In some embodiments, prescriber records and/or payer/PBM records may also be stored in the database 218. Prescriber records may include a prescriber name, a practice name, a prescriber DEA number, a prescriber license number, a prescriber phone number, a prescriber office address, etc. Payer/PBM records may include payer/PBM name, a payer/PBM identification number, a payer/PBM phone number, a payer/PBM office address, etc.

The controller 202 includes a program memory 204, a processor 210 (may be called a microcontroller or a microprocessor), a random-access memory (RAM) 212, and the input/output (I/O) circuit 216, all of which are interconnected via an address/data bus 214. It should be appreciated that although only one microprocessor 210 is shown, the controller 202 may include multiple microprocessors 210. Similarly, the memory of the controller 202 may include multiple RAMs 212 and multiple program memories 204. Although the I/O circuit 216 is shown as a single block, it should be appreciated that the I/O circuit 216 may include a number of different types of I/O circuits. The RAM(s) 212 and the program memories 204 may be implemented as semiconductor memories, magnetically readable memories, and/or optically readable memories, for example.

The program memory 204 may also contain machine-readable instructions (i.e., software), for execution by the processor 210. The software may perform the various tasks associated with operation of the back-end component 200, and may be an electronic request module 206 and a prescription drug pricing engine 208. For example, the electronic request module 206, when executed by the processor 210, may enable the processor 210 to process the electronic request generated by the electronic device 118 or pharmacy workstation 128. As described above, in some embodiments, the processor 210 (of the central processing system 110) can process the electronic request by forwarding the electronic request to the payer or PBM 114, with or without a price inquiry indicator designating the electronic request as a pricing inquiry. The processor 210 (of the central processing system 110 or the payer or PBM 114) can process the electronic request by parsing the electronic request for various elements contained in the electronic request, including the name of the prescription drug, to at least identify the prescription drug for which pricing information has been requested.

The prescription drug pricing engine 208, when executed by the processor 210, may enable the processor 210 to determine the price(s) of the prescription drug identified from the electronic request. In some embodiments, and at the very least, the processor 210 can execute the prescription drug pricing engine 208 to perform a look-up of the cash price of the identified prescription drug by searching through the database 218 that stores various prices for various prescription drugs. In some embodiments, if the electronic request contains customer information (e.g., customer name, insurance plan of the customer, customer rewards or membership number), the processor 210 can execute the prescription drug pricing engine 208 to perform a price look-up function of the co-pay price, and if applicable, the membership price, by comparing the customer information parsed from the electronic request to the customer-specific health plan coverage information stored in the database 218. The prescription drug pricing engine 208 may be equipped with engine rules to determine when to perform the price look-up function (e.g., upon receipt of the name of the prescription drug and customer-specific health plan coverage information, only if the electronic request contains a price inquiry indicator, regardless of whether the electronic request contains a price inquiry indicator), and to facilitate the actual price look-up function. For example, the processor 210 may perform the price look-up function using engine rules for determining cash price when the name of the prescription drug contained in the electronic request matches record(s) in the database 218 that contains the name of the prescription drug and the associated cash price. As another example, the processor 210 may perform the price look-up function using engine rules for determining co-pay price when the name of the prescription drug and customer information contained in the electronic request matches record(s) in the database 218 that contains the name of the prescription drug, customer-specific health plan coverage information, and the associated price. If the customer-specific health plan coverage information indicates that the prescription drug is covered (e.g., a formulary drug), the price is the co-pay price. If the customer-specific health plan coverage information indicates that the prescription drug is not covered (e.g., a non-formulary drug), the price is the cash price. As yet another example, the processor 210 may perform the price look-up function using engine rules for determining membership price when the name of the prescription drug and customer information contained in the electronic request matches record(s) in the database 218 that contains the name of the prescription drug, customer rewards or membership number, optionally the customer-specific health plan coverage information, and the associated membership price.

The prescription drug pricing engine 208 can be configured to prevent the processor 210 from creating a billing claim for prescription drug, because the prescription drug has not been prescribed by a prescriber.

Upon completion of the price look-up function, the processor 210 prepares to deliver the prescription drug pricing information back to the transmitter of the electronic request (e.g., electronic device 118, pharmacy workstation 128, central processing system 110). In some embodiments, the prescription drug pricing information may include more than one price for the prescription drug. For example, if the customer's health care plan covers the prescription drug and the customer's membership program provides discounts on the prescription drug, the prescription drug pricing information may include the cash price, co-pay price, and the membership price. The processor 210 may send (e.g. via server application 113) a notification including the prescription drug pricing information back to the transmitter (e.g., user interface application 111) of the electronic request, so that the transmitter can proceed with displaying the prescription drug pricing information for the prescription drug of interest.

While the software is depicted in FIG. 2 as including the electronic request module 206 and the prescription drug pricing engine 208, the software may include one or any number of modules accomplishing tasks related to pharmacy operation including, for example, receiving prescription orders, managing prescription workflow, etc. In some embodiments, the software may include instructions for implementing the exemplary method 300 as shown in FIG. 3 described below.

Figure 3:
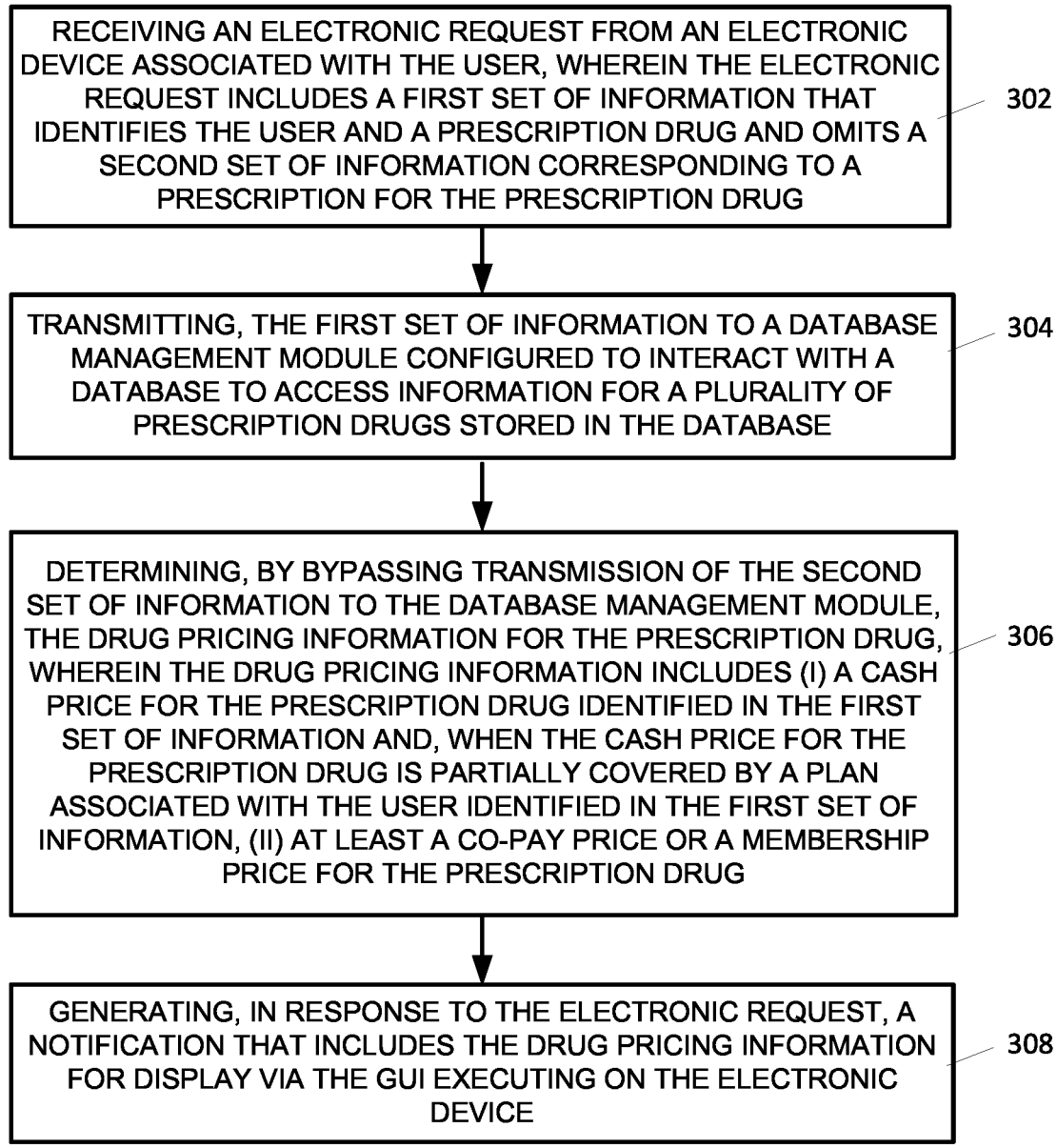
FIG. 3 illustrates a flow diagram representing an exemplary method for implementing the automated prescription drug multi-tiered pricing system in accordance with the described embodiments.

FIG. 3 illustrates a flow diagram representing an exemplary method 300 for implementing the automated prescription drug multi-tiered pricing system 100 in accordance with the presently described embodiments. The method 300 may be performed by the central processing system 110. The central processing system 110 may be configured to communicate with the workstations 128 and/or the electronic device 118, data aggregation entity 112, and/or the payer or PBM 114 to perform method 300. It should be appreciated that the method 300 is merely exemplary and may include alternative or additional functionalities.

The method 300 may begin at block 302 when the central processing system 110 (e.g., via a processor 210) receives an electronic request from an electronic device (e.g., workstation 128 and/or the electronic device 118) associated with a user. The electronic request includes a first set of information that identifies the user and a prescription drug. For example, the first set of information can include the name of the user, as well as the name of the prescription drug that the user desires to know the price of. Notably, because the customer does not have a prescription for the prescription drug, the electronic request omits a second set of information corresponding to a prescription for the prescription drug. In some embodiments, the central processing system 110 may optionally receive, via the electronic request, a pharmacy location. In this way, if the price(s) for the prescription drug vary by location of the pharmacy 120, the central processing system 110 may provide price(s) specific to the location of the pharmacy 120. Otherwise, the price(s) for the prescription drug may be the average price(s) of one or more locations of pharmacies 120. Similarly, in other embodiments, the central processing system 110 may optionally receive, via the electronic request, a dosage of the prescription drug. In this way, the price(s) for the prescription drug may reflect the dosage indicated in the electronic request.

Figure 4:
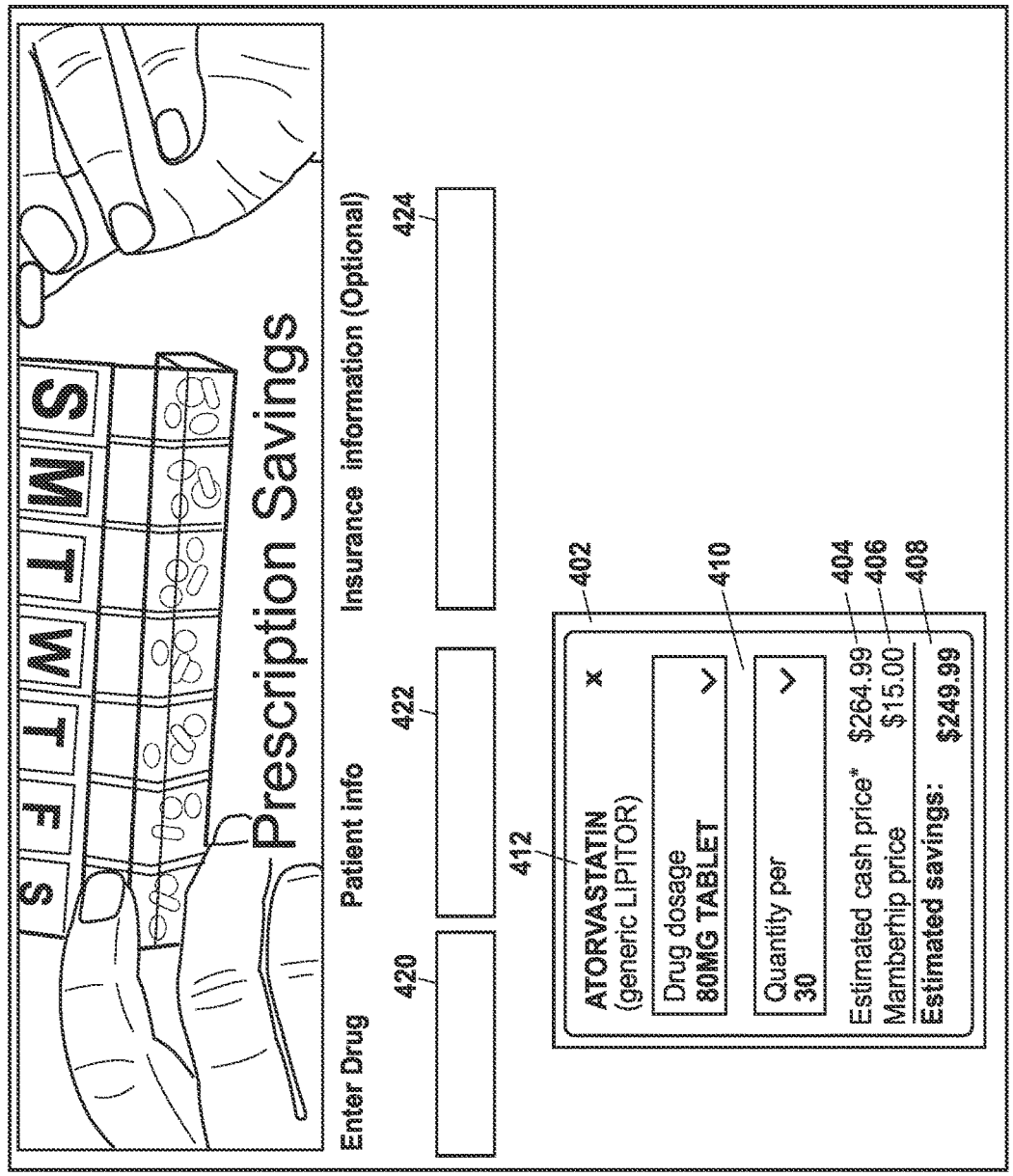
FIG. 4 illustrates an exemplary user interface associated with the automated prescription drug multi-tiered pricing system in accordance with the presently described embodiments.

With reference to FIG. 4, an electronic device associated with a user may display, upon executing user interface application 111, a GUI 400 having various user-selectable options for the user to input the first set of information (e.g., name of the drug in box 420, user's name in box 422, and insurance information in box 424). Some of the user-selectable options may be optional. For example, if the user provides the name of the drug in box 420 and the user's name in box 422, but does not provide the user's insurance information in box 424, the back-end component(s) 104 may still be able to check the user's health plan coverage information by using the user's name. It should be appreciated that additional or less user-selectable options may be presented on the GUI. For example, other user-selectable options for identifying the user or prescription drug are contemplated, such as uploading an image of an identification card of the user, providing a social security number, etc.

The user interface application 111, upon receiving the first set of information from the user via the GUI 400, may generate the electronic request. In some embodiments, the user interface application 111 can convert each element of the first set of information (e.g., a first element corresponding to the name of the prescription drug as input into box 420, a second element corresponding to the name of the user as input into box 422, a third element corresponding to the insurance information as input into box 424) to identifiers and/or XML tags corresponding to the elements, and generate the electronic request as a data stream of the identifiers and/or XML tags. It should be appreciated that this is merely one way of generating the electronic request, and that other alternative or additional suitable ways may be contemplated. After generating the electronic request, the user interface application 111 can transmit, e.g., via I/O circuit 216, the electronic request to the central processing system 110 over the digital network 130 (e.g., in block 302 of FIG. 3).

Referring back to FIG. 3, at block 304, the central processing system 110 may then transmit the first set of information to a database management module configured to interact with a database (e.g., database 218) to access information for a plurality of prescription drugs stored in the database. The central processing system 110 may transmit the first set of information in the form of a query or command having parameter values for each element of the first set of information that is pursuant to a suitable programming language (e.g., SQL) recognized by the database. With reference to FIG. 2, the database may be associated (e.g., integral) with the central processing system 110 or the payer or PBM 114. Thus, in some embodiments, the central processing system 110 need not transmit the first set of information to an entity outside of the central processing system 110. In other embodiments, the central processing system 110 may transmit the first set of information to an external entity, such as the payer or PBM 114, via the data aggregation entity 112 in some cases. In turn, the payer or PBM 114 can send the first set of information in a request to the database.

At block 306, the central processing system 110 may then determine the prescription drug pricing information for the prescription drug identified in the electronic request. Notably, the central processing system 110 may determine the prescription drug pricing information for the prescription drug without providing the second set of information corresponding to a prescription for the prescription drug to the database management module. That is, the central processing system 110 can bypass transmission of the second set of information to the database management module. The central processing system 110 and database can operate under a certain database schema, in which the database can still provide the prescription drug pricing information to the central processing system 110 without the central processing system 110 providing the second set of information to the database. As an example schema, the database management module may be configured to prevent access to the prescription drug pricing information without the second set of information unless an overriding indicator (i.e., price inquiry indicator described above) is received as part of the electronic request, and thus, the central processing system 110 may transmit the first set of information with the overriding indicator to determine the drug pricing information. As another example schema, the database management module may not require an overriding indicator from the central processing system 110.

In some embodiments, the database can have multiple schemas. For example, the database may have a first schema for accessing pricing information if the request includes a prescription for the prescription drug, and a second schema for accessing pricing information if the request does not include a prescription for the prescription drug. The database management module, when receiving the electronic request that includes overriding indicator, may be aware that the second schema should apply. In this manner, the overriding indicator can be used to select the second schema instead of the first schema, so that the database management module can retrieve prescription drug pricing information from the database according to the second schema.

In some embodiments, the central processing system 110 at block 306 may determine the prescription drug pricing information for the prescription drug identified in the electronic request by executing database management module stored in program memory 204 to compare the first set of information to a profile of the identified user that is stored in the database. The profile may correspond to one or more records stored in the database associated with the customer, such as patient profile data (e.g., patient name, Medical Record Number (MRN), patient birth date, patient address, patient phone number), customer-specific health plan coverage information data (e.g., an insurance provider along with other insurance information, an identifier of an insurance plan or membership plan associated with the patient such as an insurance group number, insurance ID number or membership ID number), and payer/PBM profile data (e.g., various prices for various prescription drugs for the identified customer). If the prescription drug identified in the electronic request is found in the payer/PBM profile data, the price for the identified prescription drug may be retrieved by the database management module.

In other embodiments, rather than the central processing system 110 comparing the first set of information to the profile of the identified user that is stored in the database, the central processing system 100 can delegate the comparison task to the payer or PBM 114, as further described in FIG. 5 below. That is, the central processing system 110 can transmit (e.g., via the I/O circuit 216) the first set of information to the database of the payer or PBM 114. Accordingly, the payer or PBM 114 can compare the first set of information to the profile of the identified user that is stored in the database to generate the drug pricing information, similar to the manner described above, and return the pricing information to the central processing system 110 (e.g., via the I/O circuit 216).

At block 308, after determining the drug pricing information, the central processing system 110 may then generate a notification that includes the prescription drug pricing information for display via the GUI executing on the electronic device. The notification can be configured to present the prescription drug pricing information in an easily digestible manner. With reference to FIG. 4, the notification 402 can be displayed via the GUI 400. The notification 402 can include the cash price 404, as well as the co-pay price (not shown) and/or membership price 406. The notification 402 can also include the difference between the cash price and the co-pay price or the membership price as an estimated savings 408. In some embodiments, the notification 402 can also include user controls 410 to adjust the dosage of the identified prescription drug 412. Adjustment of the dosage by the user can cause appropriate adjustments to the cash price 404, membership price 406, and the estimated savings 408.

Figure 5:
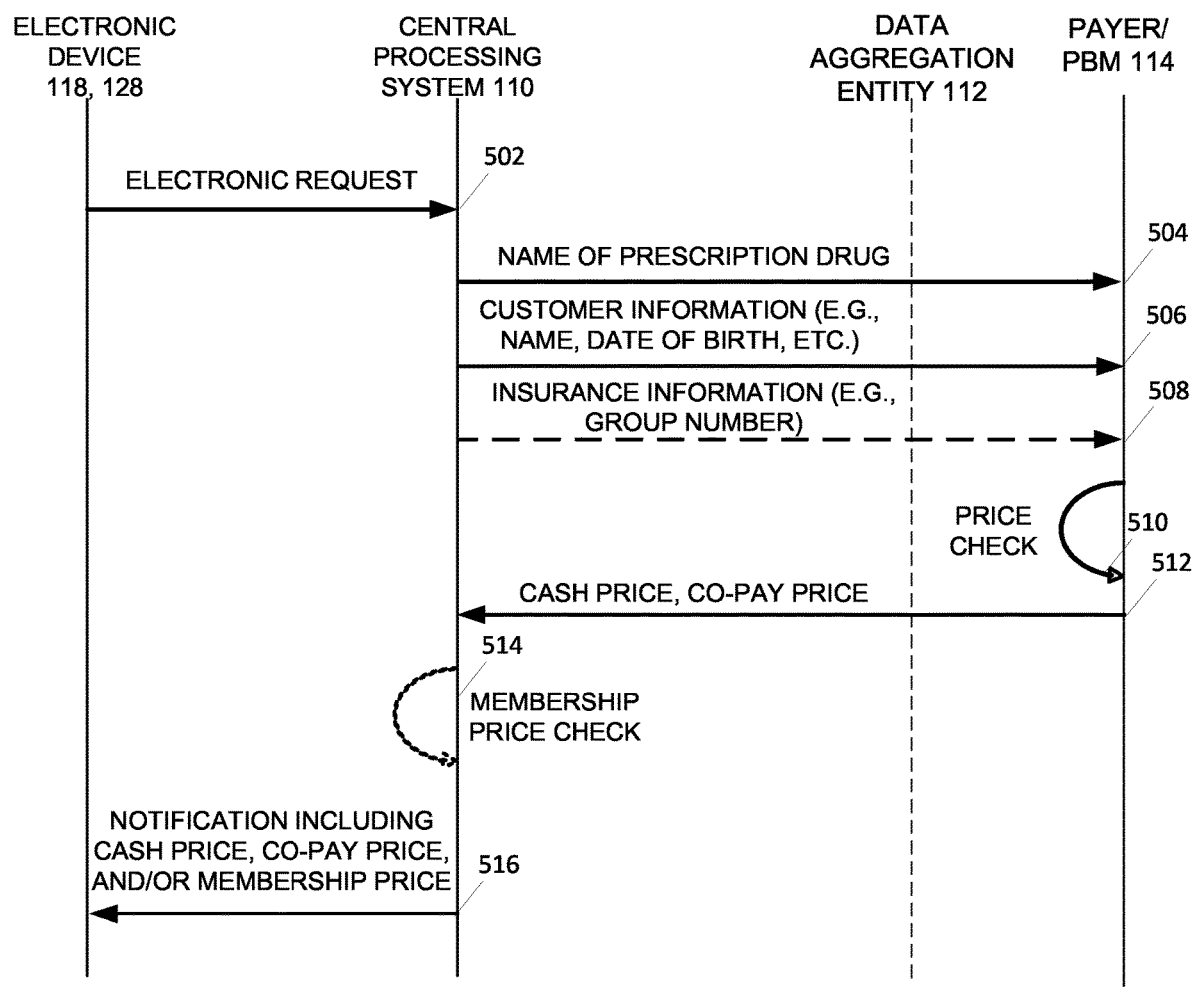
FIG. 5 illustrates a signal diagram for implementing the automated prescription drug multi-tiered pricing system in accordance with the described embodiments.

Turning now to FIG. 5, a signal diagram 500 for implementing the automated prescription drug multi-tiered pricing system is disclosed. As shown in step 502, a central processing system (e.g., central processing system 110) receives an electronic request from an electronic device (e.g., electronic device 118, pharmacy workstation 128) associated with a customer, similar to the manner described in block 302 of FIG. 3.

In step 504, the central processing system identifies the name of a prescription drug from the electronic request, and transmits the name of the prescription drug to the payer or PBM (e.g., payer or PBM 114), optionally, via an interface (e.g., data aggregation entity 112), similar to the manner described in block 304 of FIG. 3.

Similar to step 504, in step 506, the central processing system identifies customer information from the electronic request, and transmits the customer information to the payer or PBM, similar to the manner described in block 304 of FIG. 3.

Similar to step 504, in step 508, if the central processing system identifies insurance information from the electronic request, the central processing system transmits the insurance information to the payer or PBM, similar to the manner described in block 304 of FIG. 3.

In step 510, after the payer or PBM receives the name of the prescription drug, customer information, and/or insurance information from the central processing system, the payer or PBM performs a price look-up of the prescription drug.

In step 512, the payer or PBM transmits the prices of the prescription drug to the central processing system, optionally, via the interface (e.g., data aggregation entity 112). Accordingly, the central processing system determines multi-tiered drug prescription pricing information for the prescription drug, similar to the manner described in block 306 of FIG. 3.

In step 514, in some embodiments, the central processing system can determine the membership price for the prescription drug if applicable, similar to the manner described in block 306 of FIG. 3. Because the central processing system is aware of the customer information, the central processing system may be able to determine whether the customer is enrolled in a membership plan, or other discount plan (e.g., coupons).

In step 516, the central processing system can transmit, to the electronic device, a notification including the prices of the prescription drug acquired from the payer or PBM, as well as the membership price if applicable, similar to the manner described in block 308 of FIG. 3.

Accordingly, the automated prescription drug multi-tiered pricing system described herein may deliver multi-tiered pricing information for the prescription drug to the electronic device, without a prescription.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including rules, engines, applications, or instructions. These may constitute either software (e.g., code embodied on a machine-readable medium or in a transmission signal) or hardware, such as tangible processing units capable of performing certain operations and may be configured or arranged in a certain manner. In example embodiments, one or more computer component systems (e.g., central processing system, data aggregation entity, payer or PBM) or one or more hardware modules of a computer system (e.g., a processor or a group of processors) may be configured by software (e.g., an application or application portion) as a hardware module that operates to perform certain operations as described herein.

In various embodiments, a module or engine may be implemented mechanically or electronically. For example, a module or engine may comprise dedicated circuitry or logic that is permanently configured (e.g., as a special-purpose processor, such as a field programmable gate array (FPGA) or an application-specific integrated circuit (ASIC)) to perform certain operations. A module or engine may also comprise programmable logic or circuitry (e.g., as encompassed within a general-purpose processor or other programmable processor) that is temporarily configured by software to perform certain operations. It will be appreciated that the decision to implement a module or engine mechanically, in dedicated and permanently configured circuitry, or in temporarily configured circuitry (e.g., configured by software) may be driven by price and time considerations.

Accordingly, the term "module" or "engine" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which modules or engines are temporarily configured (e.g., programmed), each of the modules or engines need not be configured or instantiated at any one instance in time. For example, where the modules or engines comprise a general-purpose processor configured using software, the general-purpose processor may be configured as respective different modules or engines at different times. Software may accordingly configure a processor, for example, to constitute a particular module or engine at one instance of time and to constitute a different module or engine at a different instance of time.

Modules or engines can provide information to, and receive information from, other modules or engines. Accordingly, the described modules or engines may be regarded as being communicatively coupled. Where multiple of such modules or engines exist contemporaneously, communications may be achieved through signal transmission (e.g., over appropriate circuits and buses) that connect the modules or engines. In embodiments in which multiple modules or engines are configured or instantiated at different times, communications between such modules or engines may be achieved, for example, through the storage and retrieval of information in memory structures to which the multiple modules or engines have access. For example, one module or engine may perform an operation and store the output of that operation in a memory device to which it is communicatively coupled. A further module or engine may then, at a later time, access the memory device to retrieve and process the stored output. Modules or engines may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules or engines that operate to perform one or more operations or functions. The modules or engines referred to herein may, in some example embodiments, comprise processor-implemented modules or engines.

Similarly, the methods described herein may be at least partially processor-implemented. For example, at least some of the operations of a method may be performed by one or more processors or processor-implemented modules or engines. The performance of certain of the operations may be distributed among the one or more processors, not only residing within a single machine, but deployed across a number of machines. In some example embodiments, the processor or processors may be located in a single location (e.g., within an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules or engines may be located in a single geographic location (e.g., within an office environment or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "embodiments," "one embodiment," or "an embodiment" means that a particular element, feature, structure, or characteristic described in connection with the embodiment is included in at least one embodiment. The appearances of the phrase "embodiments" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application. This disclosure is intended to explain how to fashion and use various embodiments in accordance with the technology rather than to limit the true, intended, and fair scope and spirit thereof. The foregoing description is not intended to be exhaustive or to be limited to the precise forms disclosed. Modifications or variations are possible in light of the above teachings. The embodiment(s) were chosen and described to provide the best illustration of the principle of the described technology and its practical application, and to enable one of ordinary skill in the art to utilize the technology in various embodiments and with various modifications as are suited to the particular use contemplated. All such modifications and variations are within the scope of the embodiments as determined by the appended claims, as may be amended during the pendency of this application for patent, and all equivalents thereof, when interpreted in accordance with the breadth to which they are fairly, legally and equitably entitled.

What is claimed:

1. A server for providing drug pricing information for display on a graphical user interface (GUI) executing on an electronic device for a user, the server comprising one or more processors configured to:
   receive an electronic request from an electronic device associated with the user, wherein the electronic request includes information that identifies the user, and a prescription drug;
   transmit the information and an overriding indicator to a database management module that is configured to interact with a database to access information for the prescription drug stored in the database, the database management module further configured to prevent access to the drug pricing information without additional information unless the overriding indicator is received;
   determine, based upon the information and the overriding indicator, the drug pricing information for the prescription drug, wherein the drug pricing information includes at least a cash price for the prescription drug identified in the information;
   generate, in response to the electronic request, a notification that includes the drug pricing information for display via the GUI executing on the electronic device; and
   transmit the notification to the electronic device via a communication network.

2. The server of claim 1, wherein the information that identifies the user id automatically captured from one or more of a driver's license, an insurance card, a passport, a student identification card, a health care plan identification card, and a membership card.

3. The server of claim 1, wherein the information that identifies the user includes an identifier of a health care plan associated with the user.

4. The server of claim 1, wherein the drug pricing information includes a co-pay price and/or a membership price.

5. The server of claim 1, wherein the drug pricing information includes a price for the prescription drug that is partially covered by a health care plan.

6. The server of claim 1, wherein:
the information includes a location of a pharmacy; and
determining the drug pricing information is further based on the location of the pharmacy.

7. The server of claim 1, wherein the server is further configured to:
determine a lowest price of the prescription drug corresponding to a lowest dosage of the prescription drug, and
determine a highest price for the prescription drug corresponding to a highest dosage of the prescription drug.

8. A computer-implemented method for providing drug pricing information for display on a graphical user interface (GUI) executing on an electronic device for a user, the method comprising:
receiving, by one or more processors, an electronic request from an electronic device associated with the user, wherein the electronic request includes information that identifies the user, and a prescription drug;
transmitting, by the one or more processors, the information and an overriding indicator to a database management module that is configured to interact with a database to access information for the prescription drug stored in the database, the database management module further configured to prevent access to the drug pricing information without additional information unless the overriding indicator is received;
determining, by the one or more processors based upon the information and the overriding indicator, the drug pricing information for the prescription drug, wherein the drug pricing information includes at least a cash price for the prescription drug identified in the information;
generating, by the one or more processors based upon the electronic request, a notification that includes the drug pricing information for display via the GUI executing on the electronic device; and
transmitting, by the one or more processors, the notification to the electronic device via a communication network.

9. The computer-implemented method of claim 8, wherein the information that identifies the user id automatically captured from one or more of a driver's license, an insurance card, a passport, a student identification card, a health care plan identification card, and a membership card.

10. The computer-implemented method of claim 8, wherein the information that identifies the user includes an identifier of a health care plan associated with the user.

11. The computer-implemented method of claim 8, wherein the drug pricing information includes a co-pay price and/or a membership price.

12. The computer-implemented method of claim 8, wherein the drug pricing information includes a price for the prescription drug that is partially covered by a health care plan.

13. The computer-implemented method of claim 8, wherein:
the information includes a location of a pharmacy; and
determining the drug pricing information is further based on the location of the pharmacy.

14. The computer-implemented method of claim 8, further comprising:
determining, by the one or more processors, a lowest price of the prescription drug corresponding to a lowest dosage of the prescription drug, and
determining, by the one or more processors, a highest price for the prescription drug corresponding to a highest dosage of the prescription drug.

15. A non-transitory, tangible computer-readable medium storing machine readable instructions to provide drug pricing information for display on a graphical user interface (GUI) executing on an electronic device for a user that, when executed by one or more processors, cause the one or more processors to at least:
receive an electronic request from an electronic device associated with the user, wherein the electronic request includes information that identifies the user, and a prescription drug;
transmit the information and an overriding indicator to a database management module that is configured to interact with a database to access information for the prescription drug stored in the database, the database management module further configured to prevent access to the drug pricing information without additional information unless the overriding indicator is received;
determine, based upon the information and the overriding indicator, the drug pricing information for the prescription drug, wherein the drug pricing information includes at least a cash price for the prescription drug identified in the information;
generate, in response to the electronic request, a notification that includes the drug pricing information for display via the GUI executing on the electronic device; and
transmit the notification to the electronic device via a communication network.

16. The non-transitory, tangible computer-readable medium of claim 15, wherein the information that identifies the user id automatically captured from one or more of a driver's license, an insurance card, a passport, a student identification card, a health care plan identification card, and a membership card.

17. The non-transitory, tangible computer-readable medium of claim 15, wherein the information that identifies the user includes an identifier of a health care plan associated with the user.

18. The non-transitory, tangible computer-readable medium of claim 15, wherein the drug pricing information includes a co-pay price and/or a membership price.

19. The non-transitory, tangible computer-readable medium of claim 15, wherein the drug pricing information includes a price for the prescription drug that is partially covered by a health care plan.

20. The non-transitory, tangible computer-readable medium of claim 15, wherein the instructions, when executed by the one or more processors, further cause the one or more processors to:

determine a lowest price of the prescription drug corresponding to a lowest dosage of the prescription drug, and determine a highest price for the prescription drug corresponding to a highest dosage of the prescription drug.

* * * * *